US008720573B2

(12) United States Patent
Eriksen

(10) Patent No.: US 8,720,573 B2
(45) Date of Patent: May 13, 2014

(54) METHOD FOR SAMPLING AND ANALYSIS OF PRODUCTION FROM A SUBSEA WELL FOR MEASURING SALINITY OF PRODUCED WATER AND ALSO VOLUMETRIC RATIO BETWEEN LIQUID FRACTIONS

(75) Inventor: Egil Eriksen, Foldrøyhamn (NO)

(73) Assignee: Tool-Tech AS, Stord (NO)

(*) Notice: Subject to any disclaimer, the term of this patent is extended or adjusted under 35 U.S.C. 154(b) by 94 days.

(21) Appl. No.: 13/319,511

(22) PCT Filed: May 6, 2010

(86) PCT No.: PCT/NO2010/000171
§ 371 (c)(1),
(2), (4) Date: Jan. 20, 2012

(87) PCT Pub. No.: WO2010/131978
PCT Pub. Date: Nov. 18, 2010

(65) Prior Publication Data
US 2012/0111571 A1 May 10, 2012

(30) Foreign Application Priority Data

May 9, 2009 (NO) .................................. 20091818

(51) Int. Cl.
E21B 43/36 (2006.01)
E21B 47/00 (2012.01)

(52) U.S. Cl.
USPC ........................................................ 166/336

(58) Field of Classification Search
USPC ......... 166/336, 351, 352, 357, 250.01, 252.3, 166/267, 75.12; 702/6; 73/61.43, 61.44, 73/61.48, 61.49, 152.23, 152.28, 152.32, 73/152.42; 204/563, 573, 660, 672, 673; 210/746; 436/25

See application file for complete search history.

(56) References Cited

U.S. PATENT DOCUMENTS 3,590,919 A    7/1971  Talley, Jr.
5,962,780 A   10/1999  Prouvost
(Continued)

FOREIGN PATENT DOCUMENTS

EP             2075403 A1 *  7/2009
GB             2398523 A     8/2004
WO    WO 2008002147 A1 *  1/2008
WO         2009045111 A1    4/2009

OTHER PUBLICATIONS

International search report and written opinion for application No. PCT/NO2010/000171 dated Jul. 7, 2010.

Primary Examiner — Matthew Buck
Assistant Examiner — Stacy Warren
(74) Attorney, Agent, or Firm — Patterson & Sheridan, L.L.P.

(57) ABSTRACT

A permanent subsea sampling and analysis system is integrated into a replaceable equipment module for a choke valve of a subsea production well. The analysis system is self-contained, and separates a sample into liquid fractions consisting of crude oil, condensate and produced water and then measures the salinity of the water as well as the volumetric ratio between the liquid fractions all in the same sampling container.

7 Claims, 1 Drawing Sheet

(56) References Cited

U.S. PATENT DOCUMENTS

| | | | |
|---|---|---|---|
| 6,640,901 B1* | 11/2003 | Appleford et al. | 166/357 |
| 6,758,964 B2 | 7/2004 | Roudil et al. | |
| 7,048,060 B2 | 5/2006 | Ostergaard | |
| 7,526,407 B2 | 4/2009 | Bringedal et al. | |
| 2003/0011386 A1 | 1/2003 | Xie et al. | |
| 2003/0033866 A1* | 2/2003 | Diakonov et al. | 73/152.55 |
| 2004/0200620 A1* | 10/2004 | Ostergaard | 166/357 |
| 2007/0276603 A1 | 11/2007 | Bringedal et al. | |
| 2008/0015792 A1 | 1/2008 | Scott | |
| 2008/0116072 A1* | 5/2008 | Liverud et al. | 204/563 |
| 2011/0006790 A1* | 1/2011 | Kirkaune | 324/664 |

\* cited by examiner

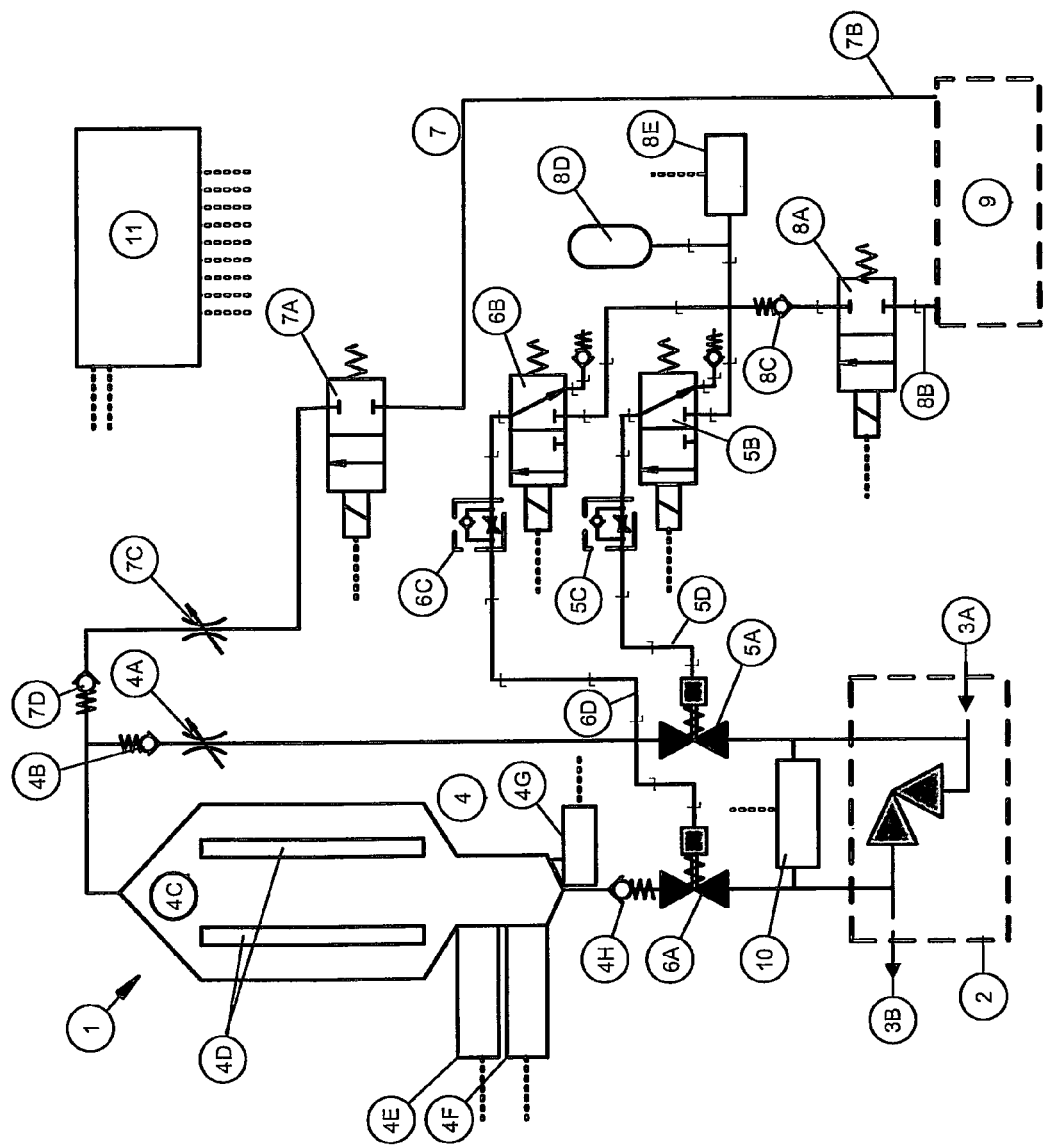

METHOD FOR SAMPLING AND ANALYSIS OF PRODUCTION FROM A SUBSEA WELL FOR MEASURING SALINITY OF PRODUCED WATER AND ALSO VOLUMETRIC RATIO BETWEEN LIQUID FRACTIONS

The invention relates to a method for sampling and analysis for determining salinity of produced water and also volumetric ratio between the liquid fractions of the well flow of a subsea production well, as stated in the preamble of the accompanying claims 1 and 2.

Usually, several subsea wells produce to a joint subsea manifold, whereby the production from several wells becomes mixed. Measurements associated with the production of a singular well must therefore be made upstream of the manifold. Normally, a multiphase flow meter is installed on the well equipment for the production from each single well. Monitoring of the salinity of the water phase is not included. This is information that the operator wants to obtain in order to update the calibration set-up of the multiphase meter. By virtue of a difference in salinity between produced water and injected water, the salinity of the water phase may also be used to reveal a possible water breakthrough from water injection into the petroleum reservoir.

The method is based on the use of a permanently installed, instrumented separation receptacle with associated valves and pipe connections forming an analysis circuit in parallel with the choke valve of the subsea well, the valve of which is located on the production outlet from the equipment mounted on the wellhead.

Prior art for determining the salinity of produced water from a singular well is represented by sampling carried out by means of a vessel operation, which carries associated limitations and expenses. The sampling is carried out using a sampling unit, which is mounted on a remotely operated vehicle (ROV). The ROV temporarily connects itself to the well equipment in order to carry out sampling via connection points on an ROV panel. The sampling system contains several receptacles for storing samples, a system consisting of different connection points for the ROV, and valves and actuators for carrying out the sampling. The samples are retrieved to the surface and are shipped to a laboratory for analysis of the salinity of the produced water.

When using a permanently installed analysis equipment, analysis of the salinity of produced water from the well may be carried out at the required or desired frequency, and without the cost associated with sampling via intervention operations carried out from a vessel, or without having to temporarily shut down the production from other wells producing to a joint subsea manifold in order to find out which well has possibly experienced a water breakthrough resulting from water injection into a reservoir.

The analysis equipment may be installed on the well equipment in connection with new subsea developments, or it may be installed on existing equipment by virtue of replacing the arrangement for the well's choke valve with a new one fitted with an analysis system.

Permanent installation of an analysis system on subsea production equipment represents a one-time phenomenon and may be done at a favorable time at which the installation is coordinated with other operations, for example a planned replacement of a subsea control module and choke valve.

When integrating the measuring instruments in parallel with the subsea well's choke valve in context of various subsea solutions, various practical adjustments are required depending on the manner in which the choke valve is integrated with the other well equipment. Generally, there are three different solutions for integrating choke valves into subsea production equipment: a choke bridge having the choke valve installed in a replaceable module between the manifold and the equipment mounted on the wellhead; a flow control module having the choke valve installed in a replaceable module on top of the equipment mounted on the wellhead; and an insert choke wherein the inside thereof may be removed or installed from the surface using a special tool system.

When a sample is to be analysed, a part of the production flow is directed into the analysis circuit, whereby the separation-and-analysis receptacle is filled with a representative sample from the production of the well. The analysis circuit is isolated from the production flow, and the sample is separated into fractions consisting of water, oil and condensate. The salinity of the produced water is determined by measuring the conductivity through the medium.

The ratio between produced water, oil and gas in the sample is recorded using an ultrasonic gauge. This measurement may be compared with measurements made with the multiphase flow meter. Data are transmitted to the surface via electronic communication and may be used to update the calibration set-up of the well's multiphase flow meter, to monitor a possible water breakthrough in context of water injection into the reservoir, and possibly to carry out other reservoir-technical analyses.

FIG. 1 shows a schematic sectional side view of the analysis system and associated process and control connections:

1 Permanent subsea sampling and analysis system
2 Choke valve of a production well
3A/B Production flow into/out of choke valve 2 installed on well-head equipment
4 Analysis circuit
4A Adjustable restriction in analysis circuit 4
4B Check valve upstream of a separation-and-analysis receptacle 4C
4C Separation-and-analysis receptacle
4D Electrostatic coalescer
4E/4F Instruments for measuring salinity of produced water (upper/lower position)
4G Level gauge operating by means of ultrasound
4H Check valve downstream of separation-and-analysis receptacle 4C
5A Gate valve upstream of separation-and-analysis receptacle 4C
5B Hydraulic control valve for actuation of gate valve 5A
5C Choke and check valve on the line for actuation of gate valve 5A
5D Hydraulic line for actuation of gate valve 5A
6A Gate valve downstream of separation-and-analysis receptacle 4C
6B Hydraulic control valve for actuation of gate valve 6A
6C Choke and check valve on the line for actuation of gate valve 6A
6D Hydraulic line for actuation of gate valve 6A
7A Isolation valve for supply of MEG (Mono Ethylene Glycol)
7B Supply of MEG
7C Adjustable restriction on MEG line
7D Check valve at connection point between MEG line (7B) and analysis circuit 4
8A Isolation valve for hydraulic supply
8B Hydraulic supply for control valves
8C Check valve downstream of isolation valve 8A for hydraulic supply
8D Accumulator on hydraulic supply 8B for dampening pressure drops in context of hydraulic consumption 8E Pressure transmitter for hydraulic supply 8B
9 Connection point for hydraulics and MEG
10 Differential-pressure transmitter for measuring pressure drops across the well's choke valve 2
11 Electronics unit for signal processing, for activation of valves, and for communication.

Typically, the analysis system (1) is integrated with a new or existing arrangement for a choke valve (2) at the production outlet (3A) from a subsea well. The system (1) is retrieved to the surface. Alternatively, the system (1) is installed on the well equipment as part of the same equipment module embodying the choke valve (2), or possibly as a separate system.

When inactive, the analysing circuit (4), together with the separation-and-analysis receptacle (4C), is to be filled with MEG (Mono Ethylene Glycol) and to be isolated from the production bore via two hydraulically actuated gate valves (5A and 6A). The analysis circuit (4) with the separation-and-analysis receptacle (4C) and the MEG supply (7B) is to be dimensioned for a full well pressure.

The hydraulic supply (8B) and also the MEG supply (7B) are taken from a connection point (9) on the subsea manifold. An isolation valve (8A) is used to open the hydraulic supply line (8B) to the control valves (5B and 6B) controlling the isolation valves (5A and 6A). Normally, the control valves may discharge the return flow into the sea when a water-based hydraulic fluid is used. When using a synthetic, hydrocarbon-based hydraulic fluid, discharge into the sea is not permitted, and the return flow is connected to the return system of the subsea control system (this is not shown in FIG. 1). A check valve (8C) is to be fitted downstream of the hydraulic isolation valve (8A). A small hydraulic accumulator (8D) and a pressure transmitter (8E) are to be installed on the hydraulic supply downstream of the check valve (8C). The purpose of the accumulator (8D) is to counteract a pressure drop from the valve operation, which may affect the rest of the hydraulic system on the subsea installation. The separation-and-analysis receptacle (4C) is filled by virtue of opening the gate valves (5A and 6A) hydraulically via the control valves (5B and 6B). The choke and check valves (5C and 6C) are installed on the control lines (5D and 6D) of the hydraulic actuators of the gate valves (5A and 6A). Normally, the gate valves (5A and 6A) are to be closed by way of spring return. The isolation valve (7A) is used to open the MEG supply (7B). The analysis circuit (4) is equipped with an adjustable restriction (4A) and also a check valve (4B), which is located upstream of the separation-and-analysis receptacle (4C), and a check valve (4H) having an opening pressure, which typically is 2 bars, and which is located downstream of the separation-and-analysis receptacle (4C). The separation-and-analysis receptacle (4C) is equipped with an electrostatic coalescer (4D).

In the lower part of the receptacle (4C) are mounted two instruments (4E and 4F) for measuring the salinity of the separated water and a level transmitter (4G) operating by means of ultrasound.

MEG is circulated out at the same time as the analysis circuit (4) with the receptacle (4C) is filled with a representative sample from the multiphase flow from the well by virtue of opening the gate valves (5A and 6A). The differential pressure across the choke valve (2), as measured with the differential-pressure transmitter (10), ensures that a part of the well flow (3A) into the choke valve (2) is directed into the analysis circuit (4) so as to fill the receptacle (4C).

Then, the analysis circuit (4) is isolated from the production flow by virtue of closing the gate valves (6A and 5A). The electrostatic coalescer (4D) ensures that the water phase is separated and sinks to the bottom of the separation-and-analysis receptacle (4C). The lower part of the receptacle (4C), within which the salinity of the separated water is measured, is to be equipped with a restriction for collection of produced water. The purpose thereof is for this part of the receptacle (4C), which is provided with two instruments (4E and 4F) for recording salinity of the separated water, to be filled even if the water fraction is relatively small.

The two instruments (4E and 4F) for measuring salinity are to measure the conductivity of the produced water and to use the measured result as an indication of the salt concentration. Two independent measurements of the salinity are to be made at the top and at the bottom, respectively, of the lower, restricted part of the separation-and-analysis receptacle (4C).

The level gauge (4G) is to measure the liquid levels and hence the volumetric ratio between the separated fractions of water, crude oil and condensate by virtue of transmitting ultrasound upwards and into the receptacle (4C) from an instrument at the underside of the receptacle (4C), and recording reflections from the boundary layers between the liquids.

The measurement data are transmitted electronically to the surface via an electronics-and-communication unit (11) connected to the instruments and controlling the hydraulic valves via current coils mounted on the valves. The electronics unit (11) and the rest of the analysis system (1) are to receive electric power supply from a connection point on the subsea installation.

Upon having received data for the salinity of produced-water salinity and the ratio between the liquid fractions, the separation-and-analysis receptacle (4C) is cleaned and preserved by replacing the contents thereof with MEG. The gate valve (6A) and the isolation valve (7A) are opened, whereby MEG is supplied to the analysis circuit (4) with the receptacle (4C) downstream of the check valve (4B). Replacement of the contents of the separation-and-analysis receptacle (4C) may be verified via the level gauge (4G). The MEG line (7B) is equipped with a restriction (7C) and a check valve (7D) upstream of the connection point to the analysis circuit (4). When the contents of the receptacle (4C) have been replaced with MEG, the gate valve (6A) and the isolation valve (7A) on the MEG supply line (7B) are closed.

The system (1) remains inactive and isolated from the process until a need arises again for controlling the salinity of the produced water from the well.

The invention claimed is:
1. A method for discontinuous use of a permanently installed system for subsea sampling and analysis for determining salinity of produced water from a single subsea well, the method comprising the steps of:
  integrating the system into a replaceable equipment module for a choke valve for subsea production systems, the system comprising an analysis circuit with a separation- and analysis receptacle equipped with an electrostatic coalescer and two instruments for measuring salinity of separated water, the instruments of which are placed in a restricted lower part of the separation-and-analysis receptacle;
  filling the analysis circuit from a well flow by opening gate valves and allowing a differential pressure across the choke valve, as measured with a differential-pressure transmitter, to set up and direct a part of the well flow into the analysis circuit, thereby filling the separation-and-analysis receptacle with a representative sample from the production of the well;
  separating the representative sample in the separation-and-analysis receptacle into fractions of condensate, crude oil and water using the electrostatic coalescer;

measuring the salinity of the separated water using the instruments and transmitting these data to a point above the water surface via electronic communication; and upon having completed the measurement of the salinity, circulating hydrocarbons and water out of the separation-and-analysis receptacle and replacing them with Mono Ethylene Glycol, which is termed MEG.

2. The method according to claim 1, further comprising the step of measuring the volumetric ratio between liquid fractions having respective liquid levels in the sample, said respective liquid levels having boundary layers therebetween.

3. A system for determining the salinity of produced water from a subsea well, comprising:

a replaceable equipment module arranged to be integrated with a choke valve of a subsea production well, the module comprising a combined separation-and-analysis receptacle;

hydraulically operated gate valves arranged upstream and downstream of the choke valve, the gate valves arranged, upon opening, to create a differential pressure across the choke valve, wherein said differential pressure is arranged to fill the separation-and-analysis receptacle with a representative sample from the production of the well;

an electrostatic coalescer arranged in the separation-and-analysis receptacle, the coalescer arranged to separate the sample into crude oil, condensate and water fractions;

the separation-and-analysis receptacle having a restricted lower part in which the water fraction settles, said restricted lower part comprising instruments for measuring the salinity of the water fraction; and transmission equipment for transmitting data to the surface.

4. The system according to claim 3, wherein the receptacle further comprises a level gauge arranged to measure the volumetric ratio between the fractions of water, crude oil and condensate, the gauge operated by transmitting ultrasound upwards and into the separation-and-analysis receptacle from an instrument at the underside of the receptacle, the ultrasound being arranged to reflect from a boundary layer between the fractions.

5. The system according to claim 3, further comprising means for discharging the representative sample from the separation-and-analysis receptacle and replacing the representative sample with Mono Ethylene Glycol.

6. The method of claim 2, wherein the method of measuring the volumetric ratio comprises:

using a level gauge to measure the respective liquid levels of the liquid fractions for calculation of the volumetric ratio between the fractions of water, crude oil and condensate by transmitting ultrasound upwards and into the separation-and-analysis receptacle from an instrument at the underside of the separation-and-analysis receptacle;

recording reflections from the boundary layers between the liquid levels; and transmitting data for calculation of the volumetric ratio between the fractions to the surface via electronic communication.

7. The method of claim 2, wherein the method of measuring the volumetric ratio comprises:

transmitting ultrasound into the separation-and-analysis receptacle;

recording reflections from the boundary layers between the liquid levels; and transmitting data for calculation of the volumetric ratio between the fractions to the surface via electronic communication.

* * * * *